(12) United States Patent
Jefferson et al.

(10) Patent No.: US 7,738,106 B2
(45) Date of Patent: Jun. 15, 2010

(54) METHOD AND SYSTEM FOR ESTIMATING SURFACE PLASMON RESONANCE SHIFT

(75) Inventors: Stanley Ted Jefferson, Palo Alto, CA (US); Gregory Douglas VanWiggeren, San Jose, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 229 days.

(21) Appl. No.: 11/838,607

(22) Filed: Aug. 14, 2007

(65) Prior Publication Data

US 2009/0046275 A1     Feb. 19, 2009

(51) Int. Cl.
*G01N 21/55* (2006.01)

(52) U.S. Cl. .............. 356/445; 356/136; 356/243.1

(58) Field of Classification Search ......... 356/128–137, 356/445–448, 243.1, 243.4
See application file for complete search history.

(56) References Cited

U.S. PATENT DOCUMENTS

| | | | | |
|---|---|---|---|---|
| 5,341,215 | A * | 8/1994 | Seher | 356/445 |
| 6,728,429 | B1 * | 4/2004 | Melman et al. | 385/12 |
| 6,734,956 | B2 * | 5/2004 | Byrne et al. | 356/128 |
| 7,233,391 | B2 * | 6/2007 | Schermer et al. | 356/246 |
| 2007/0046943 | A1 * | 3/2007 | VanWiggeren et al. | 356/445 |
| 2007/0081163 | A1 * | 4/2007 | Liang et al. | 356/445 |
| 2008/0030736 | A1 * | 2/2008 | Thrush et al. | 356/445 |
| 2008/0096241 | A1 * | 4/2008 | Lin et al. | 435/32 |
| 2009/0141376 | A1 * | 6/2009 | Smith et al. | 359/833 |

OTHER PUBLICATIONS

Knut Johnson et al.; "Surface Plasmon Resonance: Instrumental Resolution using Photo Diode Arrays," Measurement and Science Technology, vol. 11, pp. 1630-1638(2000).
Charles H. Knapp et al.; "The Generalized Correlation Method for Estimation of Time Delay," IEEE Transactions on Acoustics, Speech and Signal Processing, vol. ASSP-24, No. 4 (Aug. 1976).

* cited by examiner

*Primary Examiner*—Hoa Q Pham

(57) ABSTRACT

A surface plasmon measurement instrument measures a change in a property (e.g., refractive index) of a material layer. The method includes providing a prism with a rear surface having a metal layer disposed thereon; providing the material layer on the metal layer on the rear surface of the prism; directing a source beam through the prism toward the rear surface in a vicinity of the material layer; performing at least two sampled measurements to detect light reflected from the rear surface and to produce two corresponding data sets; transforming the data sets to a transform domain; processing the transformed data sets to estimate a sample shift between the two data sets; and determining a change in a property of the material layer using the estimated sample shift.

20 Claims, 4 Drawing Sheets

METHOD AND SYSTEM FOR ESTIMATING SURFACE PLASMON RESONANCE SHIFT

BACKGROUND

Surface plasmon resonance (SPR) sensors have become widely employed for studying biomolecular interactions. In general, SPR sensors operate according to the following principles.

At an interface between two transparent media of different refractive indices (e.g., glass and water), light coming from the side having the higher refractive index (e.g., glass) is partly reflected and partly refracted. Above a certain critical angle of incidence, $\theta_C$, no light is refracted across the interface, and total internal reflection is observed. While the incident light is totally reflected under these conditions, the electromagnetic field component penetrates a short distance (e.g., tens or hundreds of nanometers) into the medium of the lower refractive index (e.g., water), creating an exponentially decaying evanescent wave. The propagation constant of the light parallel to the surface, $k_\theta$, is:

$$k_\theta = \left(\frac{2\pi}{\lambda}\right) n_P \sin(\theta) \quad (1)$$

where: $\lambda$ is the wavelength in free space, $n_P$ is the refractive index of the material having the higher refractive index (e.g., glass) through which the light impinges on the interface, and $\theta$ is the angle of incidence of the light beam.

Meanwhile, surface plasmons are evanescent surface electromagnetic waves that propagate along a metal/dielectric interface. Since these evanescent waves propagate on the boundary of an interface between a metal layer and a dielectric layer (for example, a protein layer in a water buffer), these oscillations are very sensitive to any change near the boundary, such as the adsorption of molecules onto the metal surface. The propagation constant of the surface plasmon, ksp, can be approximated as:

$$k_{SP} \approx \left(\frac{2\pi}{\lambda}\right) \mathrm{Re}\left[\frac{(e_m n_a^2)^{1/2}}{(e_m + n_a^2)^{1/2}}\right] \quad (2)$$

where $e_m$ is the relative permittivity of the metal, $n_a$ is the refractive index of the dielectric layer on the metal (e.g., a protein layer in a water buffer), and Re[expression] denotes the real part of the expression.

These two phenomena can be combined powerfully as follows.

If the interface between two dielectric media (e.g., glass and water) is coated with a thin layer (e.g., 50 nm) of a metal (e.g., gold), and monochromatic, p-polarized light is directed onto the interface from the side having the higher refractive index, then at a specific angle of incidence, $\theta_{SP}$ ("the resonance angle"), greater than $\theta_C$, the propagation constant of the light parallel to the interface surface, $k_X$, is equal to the real part of the propagation constant of the surface plasmon, $k_{SP}$. At the resonance angle there is a resonance energy transfer between the evanescent wave and surface plasmons. This is called surface plasmon resonance (SPR). As a result of the resonance energy transfer between the evanescent wave and surface plasmons, the intensity of the reflected light at the resonance angle is sharply attenuated. If the metal layer has an appropriate thickness, then theoretically, at the resonance angle there is no reflection of the incident light.

The resonance angle may be found as the angle, $\theta$, where $k_\theta = k_X$. Substituting from equations (1) and (2) above, we find that:

$$\left(\frac{2\pi}{\lambda}\right) n_P \sin(\theta_{SP}) = \left(\frac{2\pi}{\lambda}\right) \mathrm{Re}\left[\frac{(e_m n_a^2)^{1/2}}{(e_m + n_a^2)^{1/2}}\right] \quad (3)$$

It can be seen from equation (3) that the resonance angle, $\theta_{SP}$, is dependent upon the index of refraction of the material (e.g., a biochemical material in a water solution) provided on the metal (e.g., gold) layer.

In a typical SPR biosensing experiment, one interactant in an interactant pair (i.e., a ligand or biomolecule) is immobilized on an SPR-active gold-coated glass slide which forms one wall of a thin flow-cell, and the other interactant (e.g., an analyte) in an aqueous buffer solution is induced to flow across this surface, by injecting it through this flow-cell. As the analyte binds to the ligand, for example, the accumulation of protein on the surface results in an increase in the refractive index. When light is shined through the glass slide and onto the gold surface at angles near surface plasmon resonance, the resonance angle changes very sensitively with change in the index of refraction due to the presence of biomolecules on the gold surface. This change in refractive index is measured in real time, and the result plotted as response or resonance units (RUs) versus time (a sensorgram). The extent of binding between the solution-phase interactant and the immobilized interactant can be quantified by monitoring this change in refractive index. Accordingly, SPR is capable of high sensitivity without any fluorescent or other labeling of the interactants.

In practice, a real instrument has a lateral distribution of light at the dielectric/metal interface. Furthermore, in practice the light source does not operate at just a single frequency, but has some finite bandwidth. These two factors lead to superimposed "dips" in reflectivity and a net non-zero minimum dip having a width spanning a small range of incident angles on either side of the "true resonant angle" $\theta_{SP}$ as illustrated by the reflectivity curve 10 in FIG. 1. As a result, it can be difficult to ascertain the location of the true resonance angle $\theta_{SP}$ and therefore the index of refraction of the material under test.

Algorithms have been developed for determining the minimum of the dip, corresponding to the resonance angle $\theta_{SP}$, as a function of time during a biochemical reaction. Several such algorithms are disclosed by Knut Johansen et al., "*Surface Plasm on Resonance: Instrumental Resolution using Photo Diode Arrays*," MEASUREMENT SCIENCE AND TECHNOLOGY, Vol. 11, pp. 1630-1638 (2000), which is incorporated herein by reference. Such algorithms include intensity measurements, polynomial fitting algorithms, centroid calculation algorithms, locally weighted parametric regression, and principal component regression.

However, in practice, such algorithms may produce undesirable artifacts that appear as either noise or measurement errors. As a result, the accuracy and resolution of the measurements are reduced.

What is needed, therefore, is a method of surface plasmon resonance measurement that exhibits greater sensitivity and/or lower noise. What is also needed is a surface plasmon measurement instrument that exhibits greater sensitivity and lower noise.

SUMMARY

In an example embodiment, a method is provided for measuring a change in a property of a material layer. The method includes: providing a prism with a rear surface having a metal layer disposed thereon; providing the material layer on the metal layer on the rear surface of the prism; directing a source beam through the prism toward the rear surface in a vicinity of the material layer; performing at least two sampled measurements to detect light reflected from the rear surface and to produce two corresponding data sets; transforming the data sets to a transform domain; processing the data sets to estimate a sample shift between the two transformed data sets; and determining a change in a property of the material layer using the estimated sample shift.

In another example embodiment, a system is provided for measuring a change in a property of a material layer. The system comprises: a prism with a rear surface having a metal layer disposed thereon; a light source arranged to direct a source beam through the prism toward the rear surface; a detector disposed at a position adapted to receive light from the rear surface, the detector being adapted to detect an intensity of the reflected light and to output a data set corresponding to the detected light for each measurement made by the system; and a processor adapted to receive the data sets from the detector for at least two measurements, to transform the data sets to a transform domain; to process the transformed data sets to estimate a sample shift between the two data sets; and to determine a change in a property of the material layer using the estimated sample shift.

BRIEF DESCRIPTION OF THE DRAWINGS

The example embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

DETAILED DESCRIPTION

In the following detailed description, for purposes of explanation and not limitation, example embodiments disclosing specific details are set forth in order to provide a thorough understanding of an embodiment according to the present teachings. However, it will be apparent to one having ordinary skill in the art having had the benefit of the present disclosure that other embodiments according to the present teachings that depart from the specific details disclosed herein remain within the scope of the appended claims. Moreover, descriptions of well-known apparati and methods may be omitted so as to not obscure the description of the example embodiments. Such methods and apparati are clearly within the scope of the present teachings.

Figure 1:
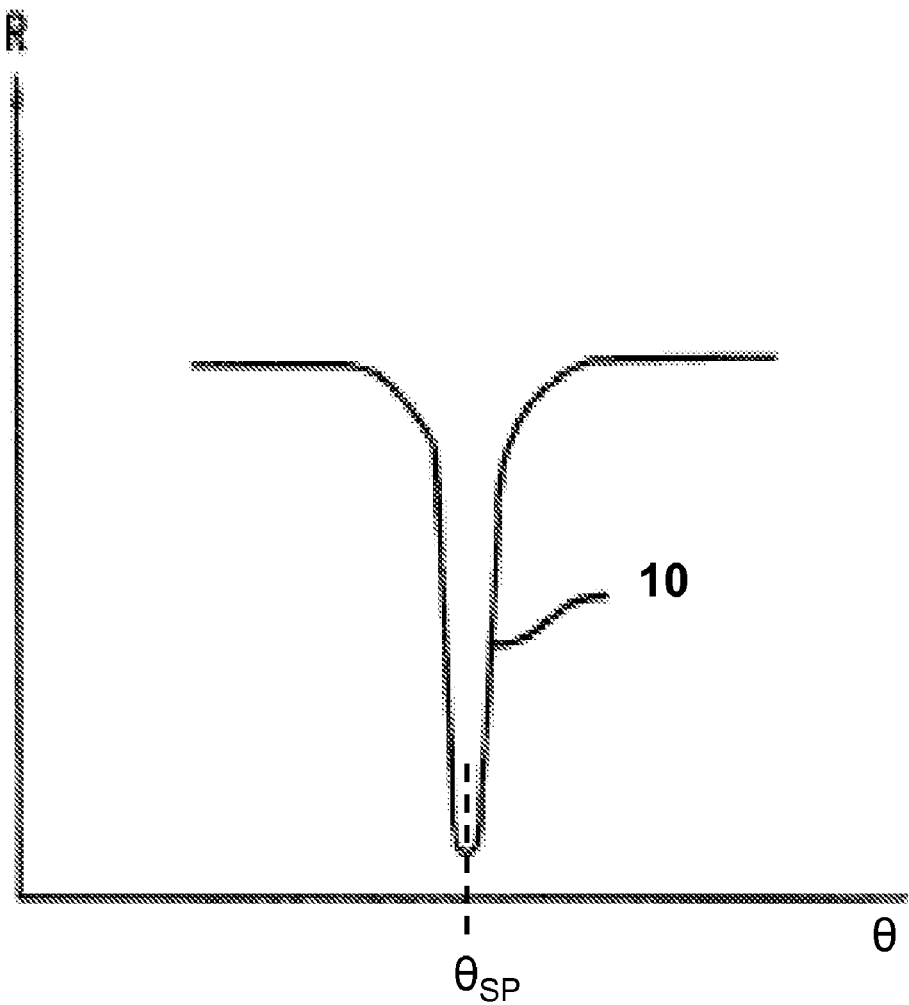
FIG. 1 illustrates a "dip" in a surface plasmon resonance measurement.
Figure 2:
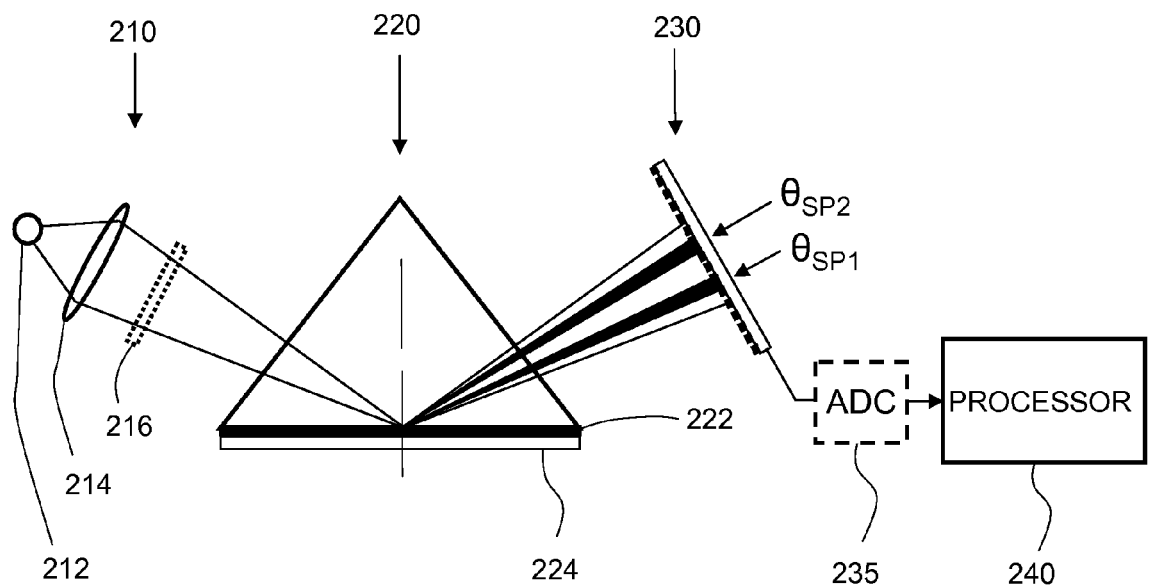
FIG. 2 is a diagram illustrating one embodiment of a surface plasmon resonance measurement instrument.

FIG. 2 is a diagram illustrating one embodiment of a surface plasmon resonance (SPR) measurement system 200.

SPR measurement system 200 includes a light source 210, a prism 220, a detector 230, an analog-to-digital converter (ADC) 235, and a processor 240.

Light source 210 includes a light generating device 212, an optical element 214, and, optionally, a polarizer 216.

In a beneficial embodiment, light generating device 212 generates monochromatic, or substantially monochromatic, light. For example, light generating device 212 may comprise a laser, or a light emitting diode. Optical element 214 receives the light from light generating device 212 and produces a source beam spanning a range of incidence angles directed toward the rear surface of prism 220. Meanwhile, in a beneficial embodiment, polarizer 216 provides a linear polarization to the source beam to output light that has a substantial p-polarization. In an alternate embodiment, polarizer 216 is omitted.

Prism 220 is optically transparent material such as glass, plexiglass, LUCITE®, etc., with an index of refraction, $n_p$. Prism 220 includes a rear surface onto which is disposed a relatively thin (e.g., 50 nm) metal layer 222. In a beneficial embodiment, the metal layer comprises gold or silver. In operation, a material layer 224 to be characterized is provided on the metal layer 222. Material layer 224 may have an index of refraction $n_a(t)$ that varies with time, for example due to the progress of a biochemical reaction taking place therein. In that case, for at least all relative times of interest, t, $n_p > n_a(t)$.

In beneficial embodiments, detector 230 comprises a two-dimensional array of light detector elements or pixels. Detector 230 may comprise a camera. In a beneficial embodiment, detector 230 comprises a charge-coupled device (CCD) array or a complementary metal oxide semiconductor (CMOS) camera of A×B pixels.

Also, in a beneficial arrangement, an analog-to-digital converter (ADC) 235 is provided to interface data from detector 230 to processor 240. However, an analog-to-digital conversion function instead may be integrated into detector 230, or provided within processor 240, in which case a separate or dedicated ADC 235 may be omitted.

Beneficially, processor 240 comprises a data sample shift estimator, as explained in greater detail below. In particular, processor 240 comprises a frequency domain data sample shift estimator. Further details will be provided below in connection with an explanation of the operation of system 200.

In some embodiments, processor 240 may include a field programmable gate array (FPGA) that is logically configured to process data from the detector 230, as explained in further detail below. In some embodiments, processor 240 may include a dedicated digital signal processor (DSP) integrated chip which is configured to execute an algorithm to process data from the detector 230, as explained in further detail below. The DSP may be configured based on data stored in a memory device, such as a programmable read only memory (PROM), a flash memory, RAM, etc. In some embodiments, processor 240 may include a general purpose programmable microprocessor executing an algorithm to process data from detector 230 in accordance with a software routine comprising instructions executable by the microprocessor. Other arrangements are possible.

In operation, system 200 may operate as follows. A source beam from light source 210 impinges on the rear surface of prism 220 in the vicinity of material layer 224, the source beam spanning a range of incidence angles. Light then reflects from the rear surface of prism 220 onto detector 230 at a range of reflection angles, θ, corresponding to the range of incidence angles. Detector 230 then outputs data corresponding to the intensity of the detected light by each detector element or pixel in detector 230.

As explained above, in theory, at the resonance angle, $\theta_{SP}$, there is no reflection of the incident light onto detector 230. Also, the index of refraction of material 224 may be determined from the resonance angle $\theta_{SP}$ according to the equations set forth above.

In a typical SPR biosensing experiment, one interactant in an interactant pair (i.e., a ligand or biomolecule) is immobilized in material layer 224, and the other interactant (e.g., an analyte) in an aqueous buffer solution is induced to flow across the surface. As the analyte binds to the ligand, for example, the accumulation of protein on the surface results in an increase in the refractive index of material later 224. When the light from light source 210 is shined onto the rear surface of prism 220 having the metal layer 222 thereon at angles near surface plasmon resonance, the resonance angle changes very sensitively with change in the index of refraction due to the presence of biomolecules on the metal layer 222. This relationship can be calibrated for system 200. Accordingly, the extent of binding between the two interactants can be determined by measuring the difference $\Delta\theta_{SP}$ between a first (or reference) resonance angle $\theta_{SP1}$ at the start of the reaction or experiment, and a second resonance angle $\theta_{SP2}$ at some point after the reaction has been initiated.

Now, consider two measurements of the light reflected from the rear surface of prism 210 to detector 230 as a function of angle, for example before and after a reaction between two (or more) interactants. For the two measurements, detector 230 in turn produces two corresponding sampled data sets, x(kT) and y(kT) (where k is a natural number and T is an interval between adjacent samples, for example, an angular interval between adjacent samples produced by adjacent detector elements or pixels). In that case, a sample shift $\tau$ indicates how far the two sets of sampled data from detector 230 are shifted apart with respect to each other. One can calculate an estimate of the sample shift, $\tau_{EST}$, between the two sampled data sets by finding the value of $\tau$ that minimizes the sum-square error:

$$\sum_{k=0}^{N} |x(kT) - y(kT - \tau)|^2 \qquad (4)$$

where N is the number of data samples in each data set. Note that the sample shift $\tau$ is a real number and may be a fraction of the (e.g., angular) sampling interval T.

However, calculating $\tau_{EST}$ directly using this least-squares approach can be quite time-consuming and may not be feasible in an application requiring fast measurement rates.

In the system 200, processor 240 comprises a data sample shift estimator that calculates an estimate of the sample shift, $\tau_{EST}$, to determine the change in the resonance angle, $\Delta\theta_{SP}$, between $\theta_{SP1}$ and $\theta_{SP2}$. However, rather than performing a least squares calculation as in Equation (4), instead, in a beneficial arrangement, processor 240 comprises a data shift estimator that determines the estimated sample shift $\tau_{EST}$ by first transforming the two sampled data sets x(kT) and y(kT) into a transform domain. In one embodiment, processor 240 performs a discrete Fourier transform (DFT) on each of the sampled data sets to transform them into the frequency domain. In alternative embodiments, other transformations may be employed instead (e.g., a Laplace transform, a Hilbert transform, a z-transform, etc.) to transform the data sets to other transform domains. The embodiment where a DFT is employed will now be explained in greater detail, but it is understood that the general principles apply when other transformations are employed, with corresponding changes to the equations and individual details.

If we represent the first sampled data set as $x_t$ for $t \in \{0, \ldots, N-1\}$, then the DFT of $x_t$, $X_k$, is found as:

$$X_k = \sum_{t=0}^{N-1} x_t e^{-jtk2\pi/N} \qquad (5)$$

A similar relationship holds between the second sampled data set, $y_t$, and $Y_k$.

In one embodiment, processor 240 transforms the two data sets $x_t$ and $y_t$ output by detector 230 into the frequency domain (e.g., by a DFT) to facilitate calculation of the estimated sample shift $\tau_{EST}$ between the two data sets.

In one embodiment, processor 240 calculates the estimated sample shift $\tau_{EST}$ as a weighted average of the sample shifts for each frequency component in the transformed data sets. In that case, $\tau_{EST}$ may be calculated as:

$$\tau_{EST} = \sum_{k=1}^{N/2} W(k) \angle (X_k / Y_k) / (k2\pi/N), \qquad (6)$$

where $\angle$(argument) denotes an angle of (argument) in radians, and W(k) is a weighting function.

In one embodiment, the weighting function, W(k), is:

$$W(k) = \begin{cases} |X_k| / \sum_{i=1}^{M} |X_i| & k = 1, \ldots, M \\ 0 & \text{otherwise,} \end{cases} \qquad (7)$$

where M is a selected value such that $M \leq N12$. The parameter M could be fixed during manufacture of system 200, or could be selected based on experience using system 200, or tailored to the characteristics of a specific resonance curve.

As explained above, the estimated sample shift $\tau_{EST}$ represents the shift between the two data sets, and can be related, through a calibration curve, to the difference in the resonance angle, $\Delta\theta_{SP}$ between a first (or reference) resonance angle $\theta_{SP1}$ at the start of a reaction or experiment, and a second resonance angle $\theta_{SP2}$ at some point after the reaction has been initiated. In one embodiment, the calibration curve may be generated during a calibration procedure for system 200. This resonance angle shift $\Delta\theta_{SP}$ in turn can be mapped to a change in the refractive index of the material layer 224 under test, permitting the extent of binding between the interactants to be quantified.

In one embodiment, processor 240 may perform a data reduction process on the data produced by detector 230 prior to processing the data, for example, prior to performing a DFT on a data set. In one embodiment, data measured by a group of detector elements (or pixels) from detector 230 is averaged to produce a data sample for each data set $x_t$ and $y_t$.

In system 200, during each measurement a plurality of pixels in detector 230 spanning a range of reflectance angles are all illuminated at the same time by the reflected light, thereby sampling the reflected beam with a sample interval of T which can be specified in radians or degrees. The data sets from the pixels in each measurement are then transformed to the frequency domain and processed to estimate the shift between data sets, and thereby the difference in the resonance angle, $\Delta\theta_{SP}$ between the two measurements. Of benefit, system 200 uses information from all of the transformed data points in the transform (e.g., frequency) domain. In contrast to other techniques which operate with only a subset of the data, typically those data points near the resonance angle, using the transformed data set provides a more complete set of information for more precisely determining the resonance angle shift.

Figure 3:
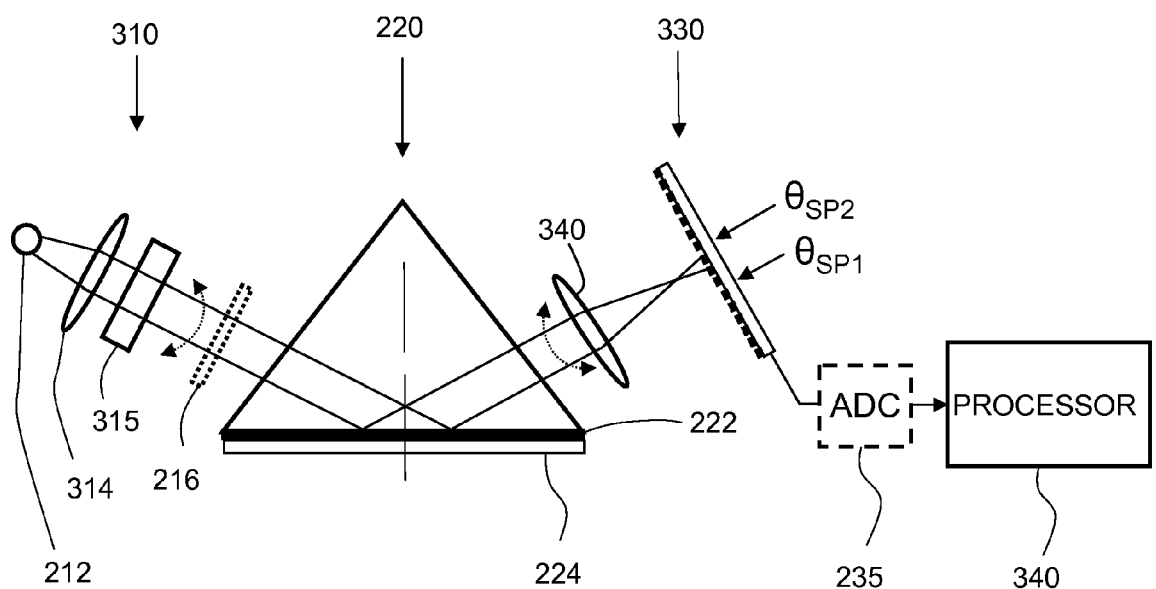
FIG. 3 is a diagram illustrating another embodiment of a surface plasmon resonance measurement instrument.

FIG. 3 is a diagram illustrating another embodiment of an SPR measurement system. In FIG. 3, like numerals to those of FIG. 2 indicate elements that are the same as the corresponding elements in FIG. 2. SPR measurement system 300 includes a light source 310, a prism 220, a detector 330, an optical element 340, an analog-to-digital converter (ADC) 235, and a processor 340.

Light source 310 includes a light generating device 212, an optical element 314, a light deflector (e.g., an acousto-optic deflector) 315, and, optionally, a polarizer 216.

In a beneficial embodiment, optical element 314 produces a collimated light beam. Meanwhile, deflector 315 scans or sweeps the incidence angle of the light beam onto the rear surface of prism 200 across a desired range of incidence angles during each sweep interval. However, during each incidence angle of the sweep, the collimated light beam illuminates a same region on the rear surface of prism 220. In one embodiment, deflector 315 includes optical elements to ensure that this happens. As the light beam is swept across the desired range of incidence angles during the sweep interval, the reflected light is swept across a corresponding range of reflection angles, θ. Meanwhile, optical element 340 images the illuminated region of the rear surface of prism 220 onto a set of detector elements or pixels in detector 330. So, as the light beam reflected by prism 220 is swept across the desired range of reflection angles, a detector element or pixel in detector 330 receives reflected light from a same spot on the rear surface of prism 220 to produce an output sequence of data samples as a function of reflection angle. Thus, from the sampled data set for a pixel or detector element, a resonance angle can be determined for the corresponding imaged spot on the rear surface of prism 220.

If the intensity of light detected by a pixel or detector element in detector 330 is sampled at a sampling interval, T, and the light beam is swept across the desired range of reflection angles θ at the sweep interval, mT (where m is an integer corresponding to the number of samples per sweep), then the pixel outputs a data sequence $x_t$, for t $\in \{0, \ldots N-1\}$, where N=mT. In one exemplary embodiment: T~0.885 ms, m=113 samples/sweep, and 1/mT=sweep rate ~10 Hz.

Now, consider two sampled measurements of the light reflected from the rear surface of prism 220 and detected by a detector element of detector 330 (for example one measurement before, and another measurement during, a reaction between two or more interactants). For the two measurements, the detector produces two corresponding sampled data sets, x(kT) and y(kT) (where k is a natural number and T is the interval between adjacent samples, for example, a time interval between adjacent samples of the pixel output). A sample shift (in this case, a sample delay) τ indicates how far the two sets of sampled data are shifted apart with respect to each other. As noted above, one can calculate an estimate of the sample shift (or delay), $\tau_{EST}$, between the two sampled data sets by finding the value of τ that minimizes the sum-square error, using equation (4) above. Note that the sample shift τ is a real number and may be a fraction of the sampling interval T (here, in time).

In system 300, processor 340 transforms the two data sets $x_t$ and $y_t$ output by detector 330 into a transform domain (e.g., the frequency domain) to facilitate calculation of the estimated sample shift $\tau_{EST}$ between the two data sets. In one embodiment, processor 340 calculates the estimated sample shift $\tau_{EST}$ as a weighted average of the sample shift for each component in the transformed data sets. In that case, $\tau_{EST}$ may be calculated using equations (6) and (7) above.

Other embodiments of sample shift estimation, particularly time delay estimation (TDE) are possible, for example, method disclosed by Charles H. Knapp et al., "*The Generalized Correlation Method for Estimation of Time Delay,*" IEEE TRANSACTIONS ON ACOUSTICS, SPEECH AND SIGNAL PROCESSING, Vol. ASSP-24, No. 4 (August 1976), which is incorporated herein by reference.

Figure 4:
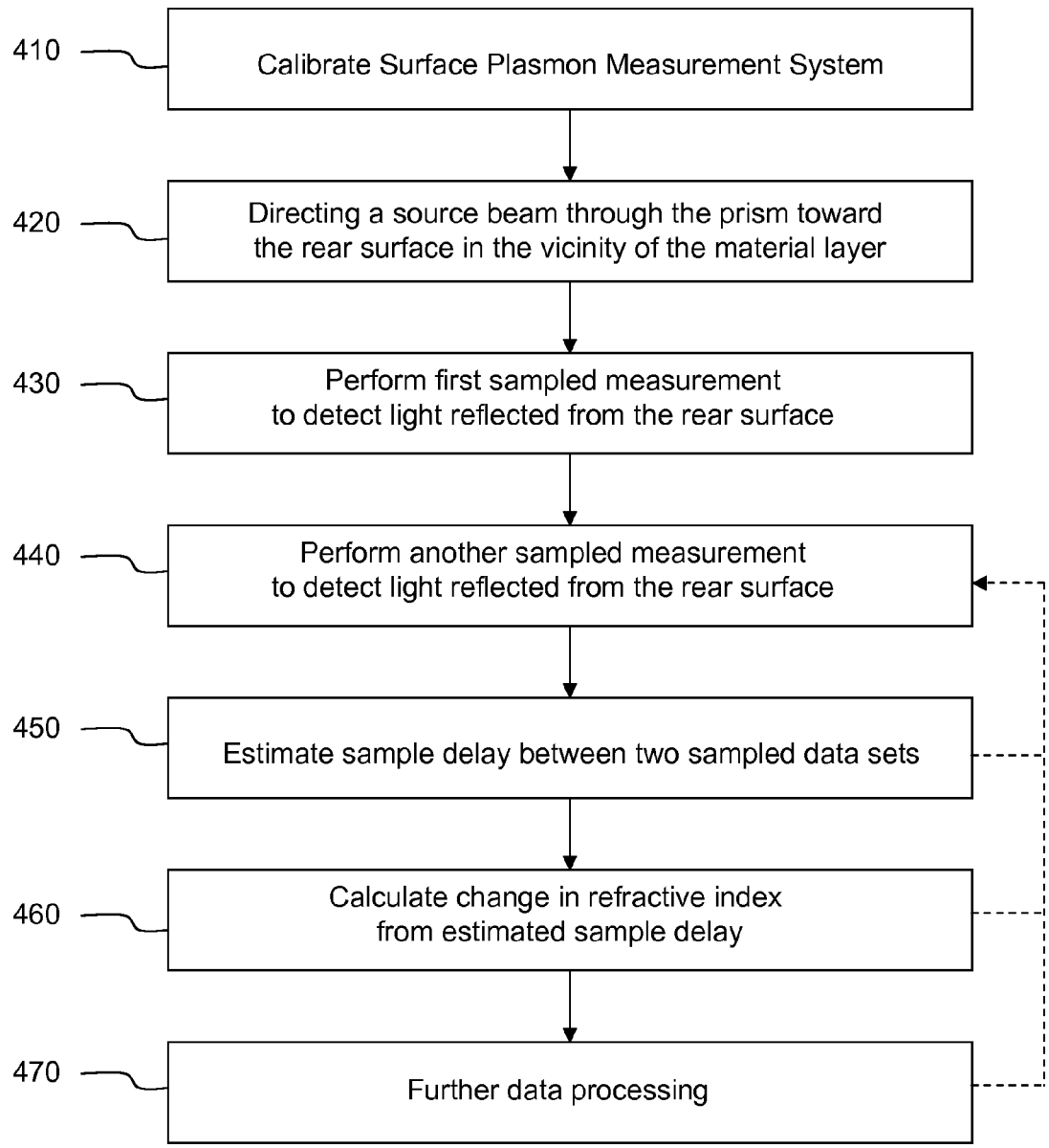
FIG. 4 is a. flowchart illustrating one embodiment of a method of measuring a change in refractive index of a layer using surface plasmon resonance.

FIG. 4 is a flowchart illustrating one embodiment of a method 400 of measuring a change in refractive index of a layer using surface plasmon resonance, in particular using SPR system 200 as generally explained above.

In a first step 410, the surface plasmon measurement system 200 is calibrated, as explained above, to produce a calibration curve for system 200.

In a second step 420, a source beam is directed through prism 220 toward its rear surface in the vicinity of material layer 224 where a biochemical reaction is arranged to occur.

In a third step 430, system 200 performs a first sampled measurement to detect light reflected from the rear surface. In a beneficial arrangement, the first sampled measurement is performed before a reaction is initiated for the material layer 224. As a result, detector 230 outputs a first set of data for a first, or reference, resonance curve.

In a fourth step 440, system 200 performs another sampled measurement to detect light reflected from the rear surface. In a beneficial arrangement, the second sampled measurement is performed at some point after a reaction is initiated for the material layer 224. As a result, detector 230 outputs a second set of data for a second resonance curve.

In a fifth step 450, processor 240 estimates the sample shift between the data sets generated in the first and second measurements. As explained above, processor 240 performs the sample shift estimation using transformed data (e.g., as a result of performing a DFT on the data).

In a sixth step 460, processor 240 calculates a change in a property in the refractive index of material layer 224 between the first and second measurements based on the estimated sample shift between the first and second data sets. In one embodiment, this property is the refractive index of material layer 224. The change in refractive index could then be used as explained above, for example to determine change in the adsorbed mass of an analyte. Alternatively, however, another property of material layer 224 could be determined—for example, the change in the adsorbed mass of an analyte could be determined from a calibration curve without the "intermediate step" of first determining the change in index of reaction.

In a seventh step 470, the data may be further processed as desired, for example, to display the resonance curves to a user, to display the change in resonance angle, etc.

Multiple resonance angle shift measurements can be made during a biochemical reaction by repeating various steps as illustrated in FIG. 4.

As explained above, with the systems and methods employing a frequency domain based sample shift estimation of data from a surface plasmon resonance measurement, a resonance angle shift produced during a biochemical reaction can be determined with accuracy and precision. In turn, this permits accurate measurement of the change in index of refraction of a material layer hosting the biochemical reaction, and finally, a measurement of the progress of a biochemical reaction under test.

While example embodiments are disclosed herein, one of ordinary skill in the art appreciates that many variations that are in accordance with the present teachings are possible and remain within the scope of the appended claims. For example, although the embodiments described above determine SPR resonance in terms of reflectivity versus angle of reflection (resonance angle), other arrangements could be provided instead, such as determining the resonance in terms of the frequency, or even the phase, of the incident light. The embodiments therefore are not to be restricted except within the scope of the appended claims.

The invention claimed is:

1. A method of measuring a change in a property of a material layer, the method comprising:
    providing a prism with a rear surface having a metal layer thereon;
    providing the material layer on the metal layer on the rear surface of the prism;
    directing a source beam through the prism toward the rear surface in a vicinity of the material layer;
    performing at least two sampled measurements to detect light reflected from the rear surface and to produce two corresponding data sets;
    transforming the data sets to a transform domain;
    processing the transformed data sets to estimate a sample shift between the two data sets; and
    determining a change in a property of the material layer using the estimated sample shift.

2. The method of claim 1, wherein performing the at least two sampled measurements comprises, during each sampled measurement:
    providing a detector array at a position adapted to receive the reflected light;
    detecting an intensity of the reflected light at each detector element of the detector array; and
    outputting the corresponding data set from the detector array.

3. The method of claim 1, wherein performing the at least two sampled measurements comprises:
    scanning the source beam onto the rear surface of the prism across a range of incidence angles;
    detecting at a detector element an intensity of the reflected light across a range of reflection angles during the scanning period; and
    outputting from the detector element a sampled data sequence corresponding to the detected intensity of the reflected light across the range of reflection angles.

4. The method of claim 1, wherein the property of the material layer is at least one of an index of refraction and an adsorbed mass of an analyte.

5. The method of claim 1, wherein processing the transformed data sets to calculate an estimate of the sample shift comprises:
    estimating a sample shift value from each component of the transformed data sets; and
    calculating a weighted average of the estimated sample shift values.

6. The method of claim 1, wherein transforming the data set to a transform domain comprises performing a discrete Fourier transform (DFT).

7. The method of claim 1, wherein transforming the data set to a transform domain comprises performing one of a Laplace transform, a Hilbert transform, and a z-transform.

8. The method of claim 1, wherein calculating a change in a property of the material layer includes comparing the estimated sample shift to calibration data for the system.

9. The method of claim 1, further comprising performing a calibration process to relate the estimated sample shift to a change in resonance angle of the reflected light from the rear surface of the prism.

10. A system for measuring a change in a property of a material layer, the system comprising:
    a prism with a rear surface having a metal layer thereon, on which metal layer the material layer can be provided;
    a light source arranged to direct a source beam through the prism toward the rear surface;
    a detector disposed at a position adapted to receive light from the rear surface at a plurality of reflection angles, the detector being adapted to detect an intensity of the reflected light and to output a data set corresponding to the detected light for each measurement made by the system; and
    a processor adapted to receive the data sets from the detector for at least two measurements, to transform the data sets to a transform domain; to process the transformed data sets to estimate a sample shift between the two data sets; and to determine a change in a property of the material layer using the estimated sample shift.

11. The system of claim 10, wherein the light source includes a deflector for scanning the source beam across a range of incidence angles with respect to the prism.

12. The system of claim 10, wherein the detector array is one of a charge-coupled device and a complementary metal oxide semiconductor (CMOS) camera.

13. The system of claim 10, wherein the processor includes one of a field programmable gate array (FPGA) and a general purpose microprocessor.

14. The system of claim 10, wherein the processor includes a digital signal processing (DSP) integrated circuit.

15. The system of claim 10, wherein the processor is adapted to determine an estimate of the sample shift by:
    estimating a sample shift value from each component of the transformed data sets; and
    calculating a weighted average of the estimated sample shift values.

16. The system of claim 10, wherein the processor is adapted to perform a discrete Fourier transform (DFT) on the data sets output from the detector.

17. The system of claim 10, wherein the processor is adapted to perform one of a Laplace transform, a Hilbert transform, and a z-transform on the data sets output from the detector.

18. The system of claim 10, wherein the property of the material layer is at least one of an index of refraction and an adsorbed mass of an analyte.

19. The system of claim 10, wherein the processor is adapted to calculate the change in the property of the material layer by comparing the estimated sample shift to calibration data for the system.

20. The system of claim 10, wherein the processor is adapted to calculate a change in refractive index of the material layer by comparing the estimated sample shift to calibration data for the system.

* * * * *